United States Patent [19]

Dusza et al.

[11] 4,209,621
[45] Jun. 24, 1980

[54] (SUBSTITUTED-PHENYL)-1,2,4-TRIAZOLO[4,3-A]-PYRIMIDINES AND (SUBSTITUTED-PHENYL)-1,2,4-TRIAZOLO[1,5-A]PYRIMIDINES

[75] Inventors: John P. Dusza, Nanuet, N.Y.; Robert A. Hardy, Jr., Ridgewood, N.J.; Jay D. Albright, Nanuet, N.Y.

[73] Assignee: American Cyanamid Company, Stamford, Conn.

[21] Appl. No.: 34,060

[22] Filed: Apr. 27, 1979

[51] Int. Cl.² .................. A61K 31/505; C07D 487/04
[52] U.S. Cl. ..................................... 544/263; 424/251; 544/315; 544/330; 544/334; 260/465 D; 260/465 F; 260/570.8 R; 260/577; 568/335; 568/336; 568/337
[58] Field of Search ......................................... 544/263

[56] References Cited

U.S. PATENT DOCUMENTS 2,443,136  6/1948  Heimbach ............................ 544/263

FOREIGN PATENT DOCUMENTS 1148629  4/1969  United Kingdom ..................... 544/263

OTHER PUBLICATIONS

Murobushi, et al., "Chemical Abstracts", vol. 49, 1955, col. 14544i to 14545b.
Shirakawa, "Chemical Abstracts", vol. 54, 1960, col. 24761h to 24763i.

*Primary Examiner*—Donald G. Daus
*Assistant Examiner*—James H. Turnipseed
*Attorney, Agent, or Firm*—Edward A. Conroy, Jr.

[57] ABSTRACT

This disclosure describes substituted 1,2,4-triazolo[1,5-a]pyrimidines and substituted 1,2,4-triazolo[4,3-a]pyrimidines which possess anxiolytic activity.

16 Claims, No Drawings

(SUBSTITUTED-PHENYL)-1,2,4-TRIAZOLO[4,3-A]-PYRIMIDINES AND (SUBSTITUTED-PHENYL)-1,2,4-TRIAZOLO[1,5-A]PYRIMIDINES

BRIEF SUMMARY OF THE INVENTION

This invention relates to new organic compounds and, more particularly, is concerned with novel substituted 1,2,4-triazolo[1,5-a]pyrimidines (I) and novel substituted 1,2,4-triazolo[4,3-a]pyrimidines (II) which may be represented by the following structural formulae:

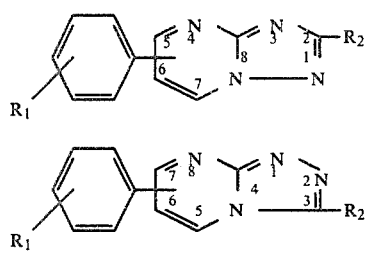

wherein $R_1$ is fluoro, chloro, trifluoromethyl or alkoxy having from 1 to 3 carbon atoms and $R_2$ is hydrogen or alkyl having from 1 to 3 carbon atoms. The invention also includes novel compositions of matter containing the above-defined compounds which are useful as anxiolytic agents and the method of meliorating anxiety in mammals therewith.

DETAILED DESCRIPTION OF THE INVENTION

The novel compounds of the present invention are in general colorless or yellow crystalline solids which are generally soluble in organic solvents such as chloroform, dichloromethane, tetrahydrofuran, acetone, N,N-dimethylformamide, acetic acid and lower alkanols.

The novel anxiolytic 7-(substituted-phenyl)-1,2,4-triazolo[1,5-a]pyrimidine compounds of the present invention may be prepared by the following reaction schemes (Scheme I). The reaction of a 2-amino-5-loweralkyltriazole (A) with a 3-di(loweralkylamino)acrylophenone (B) gives the derivatives (C), wherein $R_1$ and $R_2$ are as previously defined.

Scheme I

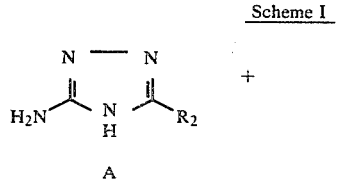

-continued
Scheme I

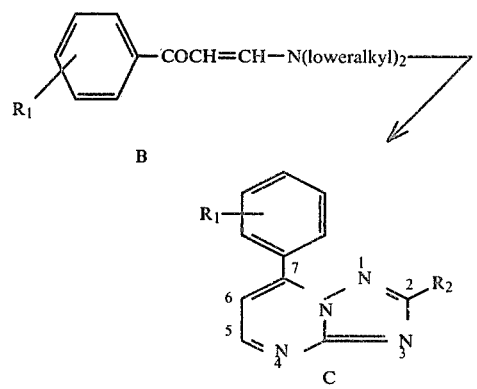

The reaction of (A) with (B) may be carried out in inert organic solvents such as lower alkanols, dioxane, tetrahydrofuran; toluene and the like, with or without acid catalysis. The preferred procedure is the reaction of (A) with (B) in refluxing glacial acetic acid for 2–24 hours.

Alternatively, the 7-(substituted-phenyl)-1,2,4-triazolo[1,5-a]pyrimidines (C) may be prepared by reacting a 2-amino-5-loweralkyltriazole (A) with a compound of formula (D) wherein X is oxygen or sulfur; $R_3$ is hydrogen, lower alkyl, an alkali metal (e.g. sodium, potassium or lithium), acetyl or benzoyl, to give the novel derivatives (C) of this invention (Scheme II). This reaction may be carried out in inert organic solvents such as lower alkanols, dioxane, tetrahydrofuran, toluene and the like with or without acid catalysis. The reaction may be carried out in glacial acetic acid and when $R_3$ is an alkali metal one equivalent of acid is added to give a compound of formula (D), wherein $R_3$ is hydrogen, as an intermediate in the ring closure to the novel compounds of formula (C).

Scheme II

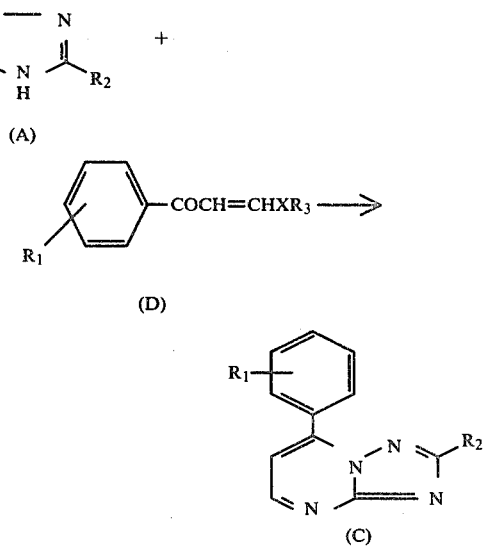

The novel 6-(substituted-phenyl)-1,2,4-triazolo[1,5-a]pyrimidines of this invention may be prepared by reaction of a 2-amino-5-loweralkyltriazole (A) with a (substituted-phenyl)formimidoylacetaldehyde of formula (E) to give the novel anxiolytic compounds (Scheme III)

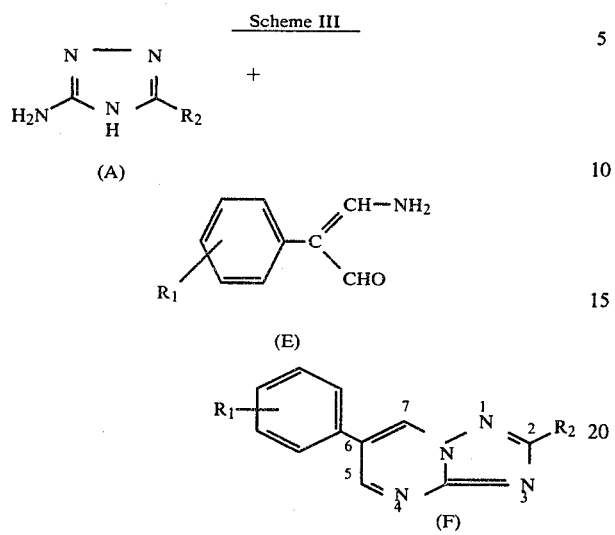

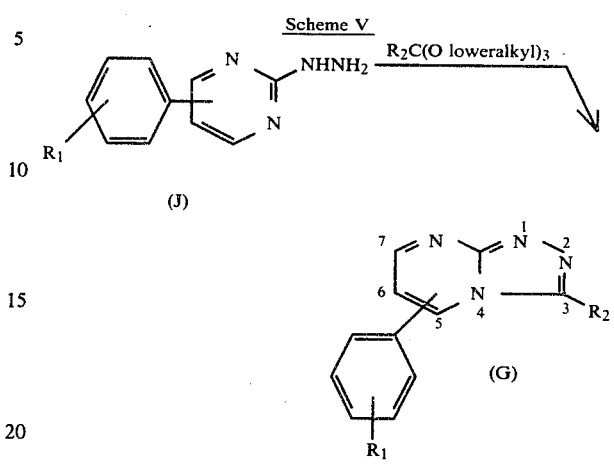

of formula (F). The reaction of (A) with (E) maybe carried out in inert organic solvents such as lower alkanols and the like with or without acid catalysis. The preferred procedure is the reaction of (A) with (E) in refluxing glacial acetic acid for 1 to 24 hours.

An alternative method for the preparation of the (substituted-phenyl)-1,2,4-triazolo[1,5-a]pyrimidine compounds (H) of this invention (Scheme IV) is the isomerization of the (substituted-phenyl)-1,2,4-triazolo[4,3-a]pyrimidine compounds (G) of this invention.

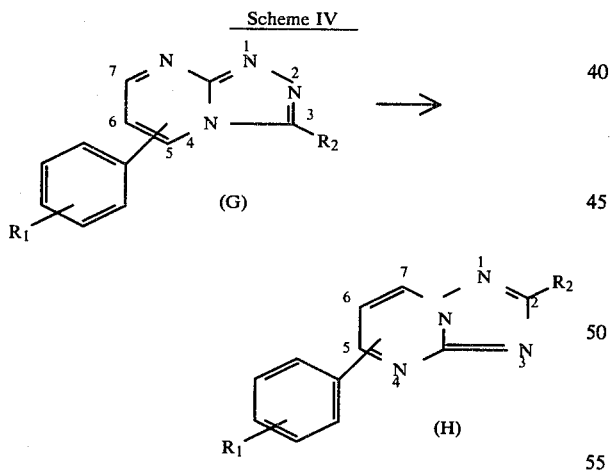

This rearrangement may be classified as a Dimroth-like rearrangement [Australian J. Chem., 30, 2515, (1977) and references therein] which has been used previously to prepare 1,2,4-triazolo[1,5-a]pyrimidines by rearrangement of 1,2,4-triazolo[4,3-a]pyrimidines (references cited above).

The preparation of novel (substituted-phenyl)-1,2,4-triazolo[4,3-a]pyrimidines (G) of this invention which exhibit anxiolytic activity is carried out by (Scheme V) reacting a 2-hydrazino-(substituted-phenyl)pyrimidine of formula (J) with lower alkyl orthoformates, lower alkyl orthoacetates or lower alkyl orthopropionates to give the compounds (G) wherein $R_1$ and $R_2$ are as previously defined.

The (substituted-phenyl)-1,2,4-triazolo[1,5-a]pyrimidines (H) may also be prepared by (Scheme VI), the ring closure of 2-hydrazino-(substituted-phenyl)pyrimidines (J) under reaction conditions in which the first formed (substituted-phenyl)-1,2,4-triazolo[4,3-a]pyrimidines (G) rearrange directly as illustrated below.

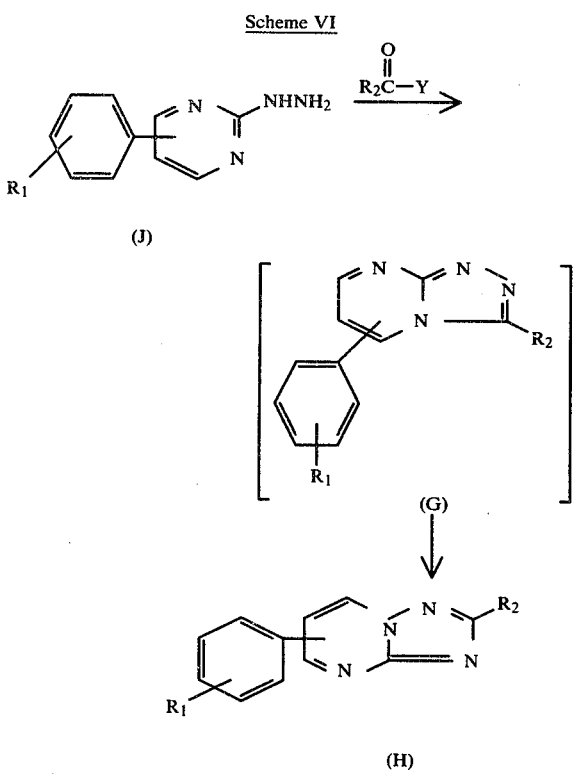

$R_2$ is as previously defined and Y is OH, halogen,

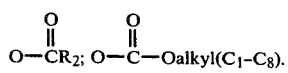

The reaction is carried out in such a manner that the acid generated in the reaction mixture along with heating causes the rearrangement of compounds (G) to compounds (H). To ensure complete rearrangement, the cyclization of (J) to (G) may be first carried out and, without isolation of intermediate (G), the reaction mixture may be heated with formic acid, acetic acid or mineral acids and the products (H) isolated by standard procedures.

The pmr spectrum of products is useful in determining whether the product is a triazolo[4,3-a]pyrimidine or a triazolo[1,5-a]pyrimidine.

The proton or methyl substituent on the triazolo ring in each series show a characteristic chemical shift; ca 9.3$\delta$ for H-3 and 2.8$\delta$ for 3-$CH_3$ in the [4,3-a] series and ca 8.5–8.6$\delta$ for H-2 and 2.6$\delta$ for 2-$CH_3$ in the [1,5-a] series. The chemical shifts the two pyrimidine proton signals (in the 8–10$\delta$ region) are also characteristically unique.

The novel compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle containing 0.5% v/v polyethylene glycol and one drop of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention have been shown to possess anxiolytic activity when tested as described above.

6-(p-Fluorophenyl)-2-methyl-1,2,4-triazolo[1,5-a]pyrimidine
6-(p-Fluorophenyl)-1,2,4-triazolo[1,5-a]pyrimidine
6-(p-Chlorophenyl)-2-methyl-1,2,4-triazolo[1,5-a]pyrimidine
6-(o-Chlorophenyl)-1,2,4-triazolo[1,5-a]pyrimidine
6-(m-Trifluoromethylphenyl)-1,2,4-triazolo[4,3-a]pyrimidine
6-(p-Fluorophenyl)-3-methyl-1,2,4-triazolo[4,3-a]pyrimidine
6-(o-Chlorophenyl)-1,2,4-triazolo[4,3-a]pyrimidine
6-(o-Chlorophenyl-3-methyl-1,2,4-triazolo[4,3-a]pyrimidine
7-(o-Fluorophenyl)-1,2,4-triazolo[1,5-a]pyrimidine
7-(m-Trifluoromethylphenyl)-1,2,4-triazolo[1,5-a]pyrimidine
2-Methyl-7-(m-trifluoromethylphenyl)-1,2,4-triazolo[1,5-a]pyrimidine
7-(o-Trifluoromethylphenyl)-1,2,4-triazolo[1,5-a]pyrimidine
7-(m-Methoxyphenyl)-1,2,4-triazolo[1,5-a]pyrimidine Another test used to measure anxiolytic activity comprises measurement of the ability of test compounds to inhibit the binding of $^3$H-diazepam to the brain receptors of warm-blooded animals. The test is described by R. F. Squires and C. Braestrup in Nature, 266, No. 21 page 732 (April 1977) and H. Mohler and T. Okada, Science, 198, 849 (1977). A modification of this test is used.

Diazepam Binding Assay

The animals used were male albino rats of the Wistar strain, weighing 150–200 g. each from Royalhart Farms. Diazepam (methyl-$^3$H; approx. 40 ci/mmol; New England Nuclear). The test compounds were solubilized in either dimethylformamide, acetic acid, ethanol or hydrochloric acid.

Frontal cortex of rats was homogenized gently in 20 volumes of ice-cold 0.32 M. sucrose, centrifuged twice at 1000 g. for 10 minutes and then recentrifuged at 30,000 g. for 20 minutes to produce a crude $P_2$-synaptosomal fraction. The $P_2$-fraction was resuspended in twice the original volume of hypotonic 50 mM. Tris.HCl (pH 7.4). The binding assay consisted of 300 $\mu$l. of the $P_2$-fraction suspension (0.350 mg.), 100 $\mu$l. of test drug and 100 $\mu$l. of $^3$H-diazepam (1.5 nM.), which was added to 1.5 ml. of 50 mM. Tris.HCl (pH 7.4). Non-specific binding controls and total binding controls received 100 $\mu$l. of diazepam (3 $\mu$M.) and 100 $\mu$l. of deionized water, respectively, in place of the test compound. Incubation for 20 minutes proceeded in ice and was terminated by filtration, under vacuum, through Whatman GF/C glass fiber filters. The filters were washed twice with 5 ml. of ice-cold 50 mM. Tris.HCl (pH 7.4) and placed in scintillation vials. After drying at 50°–60° C. for 30 minutes, 10 ml. of Beckman Ready-Solve HP was added and the radioactivity determined in a Beckman Scintillation Counter.

The percentage of inhibition of diazepam binding is calculated for each compound. A compound which exhibits the ability to inhibit binding by $\geq$20% is considered to be active.

Representative compounds of the present invention which are active when tested by the diazepam binding assay are listed below:
6-(m-trifluoromethylphenyl)-1,2,4-triazolo[1,5-a]pyrimidine
2-Methyl-6-(m-trifluoromethylphenyl)-1,2,4-triazolo[1,5-a]pyrimidine
6-(m-Fluorophenyl)-2-methyl-1,2,4-triazolo[1,5-a]pyrimidine
6-(m-Chlorophenyl)-1,2,4-triazolo[1,5-a]pyrimidine
6-(m-Chlorophenyl)-2-methyl-1,2,4-triazolo[1,5-a]pyrimidine
6-(p-Chlorophenyl)-2-methyl-1,2,4-triazolo[1,5-a]pyrimidine
6-(m-Trifluoromethylphenyl)-1,2,4-triazolo[4,3-a]pyrimidine
3-Methyl-6-(m-trifluoromethylphenyl)-1,2,4-triazolo[4,3-a]pyrimidine
6-(m-Chlorophenyl)-3-methyl-1,2,4-triazolo[4,3-a]pyrimidine
7-(m-Trifluoromethylphenyl)-1,2,4-triazolo[1,5-a]pyrimidine
2-Methyl-7-(m-trifluoromethylphenyl)-1,2,4-triazolo[1,5-a]pyrimidine 2-Ethyl-7-(m-trifluoromethylphenyl)-1,2,4-triazolo[1,5-a]pyrimidine Another test which can be used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200–240 g. each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 or 60 minutes each rat was placed in individual black plexiglass chambers. A 10% dextrose solution was available ad libitum from a tap located in the rear of the chamber. A 0.3 milliampere constant current 60 Hz pulsed DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the shocks received by the test group are significantly different from the control group by the Mann-Witney U test.

The novel compounds of the present invention have been found to be highly useful for meliorating anxiety in mammals when administered in amounts ranging from about 0.1 mg. to about 20.0 mg./kg. of body weight per day. A preferred dosage regimen for optimum results would be from about 0.5 mg. to about 10.0 mg./kg. of body weight per day. Such dosage units employed are from about 5 to about 100 mg. of active compound. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1 o-Trifluoromethylphenylacetonitrile

A mixture of 75 g. (0.31 mole) of o-trifluoromethylbenzyl bromide, 120 g. (0.55 mole) of potassium cyanide, 150 ml. of water and 600 ml. of absolute ethanol is stirred and heated under reflux for 20 hours. The reaction mixture is diluted with 4 liters of water and is extracted with 500 ml. of ether. The extract is dried over anhydrous potassium carbonate and evaporated. Distillation gives 45 g. of the desired product b.p. 103°–105° C./10 mm.

m.p. 161°–163° C. Reference: D. J. Brown and T. C. Lee, J. Chem. Soc. (C), 214 (1970).

The procedure described above is used to prepare the compounds listed in Table I.

Table I

Formylphenylacetonitriles *

| Name | $R_1$ | m.p. °C. | Crystallization Solvent |
|---|---|---|---|
| α-Formyl-p-chlorophenylacetonitrile | p-Cl | 163–165 | Acetone/Hexane |
| α-Formyl-p-fluorophenylacetonitrile | p-F | 146–147 | Acetone/Hexane |
| α-Formyl-m-chlorophenylacetonitrile | m-Cl | 166–167 | Acetone/Hexane |
| α-Formyl-m-fluorophenylacetonitrile | m-F | 143–146 | Hexane |
| α-Formyl-m-trifluoromethylphenylacetonitrile | m-CF$_3$ | 88–92 | Acetone/Hexane |
| α-Formyl-o-chlorophenylacetonitrile | o-Cl | 118–120 | Acetone/Hexane |
| α-Formyl-p-trifluoromethylphenylacetonitrile | p-CF$_3$ | 149–151 | Hexane |

* These compounds are variously named as formylphenylacetonitriles [J. Chem. Soc. (C), 214 (1970)] and phenylmalonaldehydronitriles (Chemical Abstracts) for the cyano-aldehyde tautomer; or as 3-hydroxy-2-phenylacrylontriles for the hydroxymethylene tautomer.

Using the procedure described above the following compounds are prepared;

m-Trifluoromethylphenylacetonitrile, b.p. 62°–67° C./2 mm.;

p-Trifluoromethylphenylacetonitrile, b.p. 88°–100° C./2 mm.

EXAMPLE 2

α-Formylphenylacetonitrile

A 20.0 g. amount of sodium hydride (50% in oil) is added portionwise with stirring to a solution of 20.0 g. of phenylacetonitrile and 40.0 ml. of ethyl formate in 200 ml. of sodium dried benzene. The mixture is heated on a steam bath to start the reaction and after the vigorous reaction has subsided, the mixture is heated on the steam bath for 2 hours with stirring. Ethanol is then added dropwise to decompose the excess sodium hydride. The mixture is then swamped with n-hexane and the precipitate is collected and washed with n-hexane. The precipitate is suspended in water then an excess of dilute hydrochloric acid is added and the product is extracted with ether. The ether extracts are dried and evaporated. The residue is crystallized from acetone-n-hexane to give 12.0 g. of the product of the Example

EXAMPLE 3

(Phenyl)formimidoylacetaldehyde

A mixture of 20 g. of formylphenylacetonitrile, Raney nickel (four teaspoonsful; washed with distilled water until neutral) and 200 ml. of ethanol is shaken in an atmosphere of hydrogen until somewhat more than the theoretical amount of hydrogen is utilized. The catalyst is filtered off and the filtrate is evaporated. The residue is crystallized from ethanol/benzene to give 18.0 g. of the product of the Example, m.p. 80°–82° C. Reference: J. Chem. Soc. (C), 214 (1970); J. Am. Chem. Soc., 73, 3763 (1951).

The literature procedure described above is used to prepare the compounds listed in Table II.

Table II (Phenyl)formimidoylacetaldehydes *

| Name | $R_1$ | m.p. °C. | Crystallization Solvent |
|---|---|---|---|
| (p-Chlorophenyl)formimidoylacetaldehyde | p-Cl | 96–99 | Acetone/Hexane |
| (o-Chlorophenyl)formimidoylacetaldehyde | o-Cl | 106–108 | Acetone/Hexane |
| (p-Fluorophenyl)formimidoylacetaldehyde | p-F | 91–94 | Benzene |
| (m-Chlorophenyl)formimidoylacetaldehyde | m-Cl | 96–99 | Acetone/Hexane |
| (p-Trifluoromethylphenyl)formimidoylacetaldehyde | p-CF$_3$ | 132–133 | Acetone/Hexane |
| (m-Trifluoromethylphenyl)formimidoylaldehyde | m-CF$_3$ | 62–66 | Hexane |
| (m-Fluorophenyl)formimidoylacetaldehyde | m-F | 93–96 | Benzene |

* These compounds are variously named as (phenyl) formimidoylacetaldehydes (Chemical Abstracts) or iminophenylacetaldehydes for the iminoaldehyde tautomer; or as 3-amino-2-phenylacroleins as the aminomethylene-phenyl-acetaldehyde.

EXAMPLE 4

5-Phenyl-2-pyrimidinol

A mixture of 20.0 g. of (phenyl)formimidoylacetaldehyde and 5.0 g. of urea is heated under reflux in 50 ml. of ethanol and 10 ml. of concentrated hydrochloric acid for 5 hours. The cooled mixture is swamped with 20% aqueous ammonium hydroxide and the precipitate is collected and washed with water. The precipitate is crystallized from ethanol to give 8.0 g. of the product of the Example, m.p. 239°–241° C.

EXAMPLE 5

5-(p-Chlorophenyl)-2-pyrimidinol

A mixture of 20.0 g. of (p-chlorophenyl)formimidoylacetaldehyde and 5.0 g. of urea is heated under reflux in 50 ml. of ethanol and 10 ml. of concentrated hydrochloric acid for 5 hours. The reaction mixture is worked up as described in Example 4 and the product is crystallized from ethanol to give 13.0 g. of a solid. The solid in 260 ml. of ethanol and 13 ml. of concentrated hydrochloric acid is heated under reflux for 16 hours. The reaction mixture is cooled and the material which is separated is collected and dissolved in a minimum of dimethyl sulfoxide. Dilute ammonium hydroxide (20%) is added and the product is collected, washed with water, ethanol, and ether to yield 8.78 g. of the product of the Example, m.p. 324°–327° C.

EXAMPLE 6

5-(p-Fluorophenyl)-2-pyrimidinol

A mixture of 40.0 g. of (p-fluorophenyl)-formimidoylacetaldehyde and 10.0 g. of urea is heated under reflux in 100 ml. of ethanol containing 20 ml. of concentrated hydrochloric acid for 5 hours. The reaction mixture is worked up as described in Example 5 and the product is crystallized from ethanol to give 25.6 g. of (β-formyl-p-fluorostyryl)urea.

A mixture of 12.0 g. of the preceding compound, 100 ml. of ethanol and 10 ml. of concentrated hydrochloric acid is heated under reflux for 18 hours. The mixture is treated as described in Example 5 to yield 7.66 g. of the product of the Example, m.p. 310°–318° C.

EXAMPLE 7

5-(m-Chlorophenyl)-2-pyrimidinol

By the procedure described in Example 4, (m-chlorophenyl)formimidoylacetaldehyde is reacted with urea to give the product of the Example (recrystallized from ethanol), m.p. 235°–236° C.

EXAMPLE 8

5-(o-Chlorophenyl)-2-pyrimidinol

By the procedure described in Example 4 (o-chlorophenyl)formimidoylacetaldehyde is reacted with urea to give the product of the Example (recrystallized from ethanol), m.p. 232°–233° C.

EXAMPLE 9

5-(p-Trifluoromethylphenyl)-2-pyrimidinol

By the procedure described in Example 4, (p-trifluoromethylphenyl)formimidoylacetaldehyde is reacted with urea to give the product of the Example (recrystallized from ethanol), m.p. 271°–273° C.

EXAMPLE 10

5-(m-Trifluoromethylphenyl)-2-pyrimidinol

By the procedure described in Example 4, (m-trifluoromethylphenyl)formimidoylacetaldehyde is reacted with urea to give the product of the Example (recrystallized from ethanol), m.p. 283°–285° C.

EXAMPLE 11

5-(m-Fluorophenyl)-2-pyrimidinol

By the procedure described in Example 4, (m-fluorophenyl)formimidoylacetaldehyde is reacted with urea to give the product of the Example (recrystallized from methanol), m.p. 259°–261° C.

EXAMPLE 12

2-Chloro-5-phenylpyrimidine

A mixture of 8.7 g. of 5-phenyl-2-pyrimidinol and 90 ml. of phosphorus oxychloride is heated under reflux for 5 hours. The residue obtained by evaporation of solvent is dissolved in water and to this solution is added an excess of aqueous sodium bicarbonate. The product is extracted in methylene chloride and the dried extract is evaporated. A solution of the residue in methylene chloride is passed through a short column of alumina (Woelm, Activity II) and the residue obtained by evaporation of the eluate is collected with the aid of hexane to give 6.0 g. of 2-chloro-5-phenylpyrimidine, m.p. 130°–132° C.

The procedure described above is used to prepare the 2-chloro-5-(substituted phenyl)pyrimidines listed in Table III.

Table III

2-Chloro-5-(substituted phenyl)pyrimidines

| Name | R$_1$ | m.p. °C. | Crystallization Solvent |
|---|---|---|---|
| 2-Chloro-5-(m-chlorophenyl)pyrimidine | m-Cl | 118–120 | Acetone/Hexane |
| 2-Chloro-5-(p-fluorophenyl)pyrimidine | p-F | 172–175 | Hexane - After Partition Chromatography with Diatomaceous Earth |
| 2-Chloro-5-(p-chlorophenyl)pyrimidine | p-Cl | 214–217 | Hexane - After Partition Chromatography with Diatomaceous Earth |
| 2-Chloro-5-(p-trifluoromethylphenyl)pyrimidine | p-CF$_3$ | 181–183 | Benzene/Petroleum Ether |
| 2-Chloro-5-(o-chlorophenyl)pyrimidine | o-Cl | 151–152 | Acetone/Hexane |
| 2-Chloro-5-(m-trifluoromethylphenyl)pyrimidine | m-CF$_3$ | 136–138 | Hexane |
| 2-Chloro-5-(m-fluorophenyl)pyrimidine | m-F | 140–141 | Acetone/Hexane |

EXAMPLE 13

2-Hydrazino-5-phenylpyrimidine

To a solution of 5.4 g. of 2-chloro-5-phenylpyrimidine in 25 ml. of pyridine is added 25 ml. of hydrazine hydrate. The mixture is heated on a steam bath for one hour with occasional swirling. Water is added and the material that is separated is collected and crystallized from methanol to give 4.5 g. of the product of the Example, m.p. 155° C.

The procedure described above is used to prepare the 2-hydrazino-5-(substituted phenyl)pyrimidines of Table IV.

EXAMPLE 15

3-Methyl-6-phenyl-1,2,4-triazolo[4,3-a]pyrimidine

A mixture of 3.0 g. of 2-hydrazino-5-phenylpyrimidine and 30 ml. of triethyl orthoacetate is heated under reflux overnight. The material which separates is collected, washed with hexane, and crystallized from ace- Table IV 2-Hydrazino-5-(substituted phenyl)pyrimidines

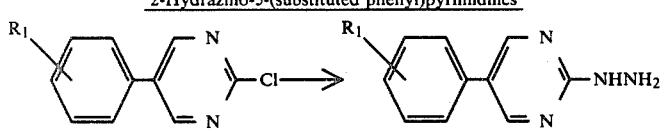

| Compound | $R_1$ | m.p. °C. | Crystallization Solvent |
|---|---|---|---|
| 2-Hydrazino-5-(p-fluorophenyl)pyrimidine | p-F | 186–187 | Methanol |
| 2-Hydrazino-5-(p-chlorophenyl)pyrimidine | p-Cl | 180–183 | Methanol |
| 2-Hydrazino-5-(m-chlorophenyl)pyrimidine | m-Cl | 167–169 | Acetone/Hexane |
| 2-Hydrazino-5-(o-chlorophenyl)pyrimidine | o-Cl | 163–165 | — |
| 2-Hydrazino-5-(p-trifluoromethylphenyl)pyrimidine | p-$CF_3$ | 170–171 | Ethanol |
| 2-Hydrazino-5-(m-fluorophenyl)pyrimidine | m-F | 165–167 | Methanol |
| 2-Hydrazino-5-(m-trifluoromethylphenyl)pyrimidine | m-$CF_3$ | 101–102 | Benzene |

EXAMPLE 14

6-Phenyl-1,2,4-triazolo[4,3-a]pyrimidine

A mixture of 2.5 g. of 2-hydrazino-5-phenylpyrimidine and 25 ml. of triethyl orthoformate is heated for 16 hours under reflux. The material that separates is collected and crystallized from ethanol to give 1.5 g. of the product of the Example, m.p. 231° C.

tone-hexane to give 2.2 g. of the product of the Example, m.p. 199°–200° C.

The following Examples for the preparation of 6-(substituted phenyl)-1,2,4-triazolo[4,3-a]pyrimidines which are listed in Table V, are prepared by the procedures described in Examples 14 and 15.

Table V 6-(Substituted phenyl)-1,2,4-triazolo[4,3-a]pyrimidines

| Example | Compound | Procedure used | $R_1$ | $R_2$ | m.p. °C. | Crystallization Solvent |
|---|---|---|---|---|---|---|
| 16 | 6-(p-Fluorophenyl)-3-methyl-1,2,4-triazolo[4,3-a]pyrimidine | Example 15 | p-F | $CH_3$ | 218–221 | Acetone |
| 17 | 6-(p-Chlorophenyl)-3-methyl-1,2,4-triazolo[4,3-a]pyrimidine | Example 15 | p-Cl | $CH_3$ | 252 | Acetone |
| 18 | 6-(m-Chlorophenyl)-3-methyl-1,2,4-triazolo[4,3-a]pyridimine | Example 15 | m-Cl | $CH_3$ | 218–220 | Ethanol |
| 19 | 6-(m-Chlorophenyl)-1,2,4-triazolo[4,3-a]pyrimidine | Example 14 | m-Cl | H | 231–232 | Ethanol |
| 20 | 6-(o-Chlorophenyl)-1,2,4-triazolo[4,3-a]pyrimidine | Example 14 | o-Cl | H | 178–180 | Ethanol |
| 21 | 6-(o-Chlorophenyl)-3-methyl-1,2,4-triazolo[4,3-a]pyrimidine | Example 15 | o-Cl | $CH_3$ | 196–198 | Hexane |
| 22 | 6-(m-Trifluoromethylphenyl)-1,2,4-triazolo[4,3-a]pyrimidine | Example 14 | m-$CF_3$ | H | 233–234 | Hexane |
| 23 | 3-Methyl-6-(m-trifluoromethylphenyl)-1,2,4-triazolo[4,3-a]pyrimidine | Example 15 | m-$CF_3$ | $CH_3$ | 182–184 | Hexane |
| 24 | 6-(p-Trifluoromethylphenyl)-1,2,4-triazolo[4,3-a]pyrimidine | Example 14 | p-$CF_3$ | H | 283–285 | Acetone |
| 25 | 6-(p-Fluorophenyl)-1,2,4-triazolo[4,3-a]pyrimidine | Example 14 | p-F | H | 280–282 | Acetone |
| 26 | 3-Methyl-6-(p-trifluoromethylphenyl)-1,2,4-triazolo[4,3-a]pyrimidine | Example 15 | p-$CF_3$ | $CH_3$ | 204–206 | Acetone/Petroleum Ether |
| 27 | 6-(m-Fluorophenyl)-1,2,4-triazolo[4,3-a]pyrimidine | Example 14 | m-F | H | 202–204 | Ethanol/Hexane |
| 28 | 6-(m-Fluorophenyl)-3-methyl-1,2,4-triazolo[4,3-a]pyrimidine | Example 15 | m-F | $CH_3$ | 198–200 | Acetone/Hexane |

EXAMPLE 29

6-(Phenyl)-1,2,4-triazolo[1,5-a]pyrimidine

A mixture of 1.0 g. of 6-(phenyl)-1,2,4-triazolo[4,3-a]pyrimidine and 10 ml. of 97% formic acid is refluxed for 5 hours and the excess formic acid is removed under reduced pressure. The solid residue is collected, washed with hexane and recrystallized from glacial acetic acid to give the product as crystals, m.p. 164°–167° C.

EXAMPLE 30

6-(Phenyl)-1,2,4-triazolo[1,5-a]pyrimidine

An equimolar mixture of (phenyl)formimidoylacetaldehyde and 3-amino-1,2,4-triazole in glacial acetic acid (5 ml. acetic acid to 0.01 mole of reagents) is refluxed for 2 hours and allowed to cool to room temperature. The solid which separates is collected, washed with glacial acetic acid and dried. The solid is recrystallized from glacial acetic acid to give the product, m.p. 164°–167° C.

The following Examples for the preparation of 6-(substituted phenyl)-1,2,4-triazolo[1,5-a]pyrimidines which are listed in Table VI, are prepared by the procedures described in Examples 29 and 30.

EXAMPLE 42

3-Hydroxy-3'-(trifluoromethyl)acrylophenone sodium salt

A mixture of 100 ml. of diethyl ether, 3.36 g. of sodium hydride (60% in oil), 7.4 g. of ethyl formate and 18.8 g. of m-trifluoromethylacetophenone is refluxed with vigorous stirring for 2 hours. The mixture is cooled and the precipitate is recovered by filtration giving 14.6 g. of the desired product, m.p. 200°–201° C.

EXAMPLE 43

3-Hydroxy-3'-(trifluoromethyl)acrylophenone acetate

A suspension of 12.0 g. of 3-hydroxy-3'-(trifluoromethyl)acrylophenone sodium salt in 75 ml. of dioxane and 10 ml. of acetic anhydride is stirred at room temperature for 2 hours and then poured into water. The precipitate is collected by filtration, dissolved in methylene chloride and then passed through a hydrous magnesium silicate column and crystallized from methylene chloride-hexane to give the desired product, m.p. 55°–57° C.

EXAMPLE 44

3-Amino-5-ethylpyrazole-4-carbonitrile

Table VI
6-(Substituted phenyl)-1,2,4-triazolo[1,5-a]pyrimidines

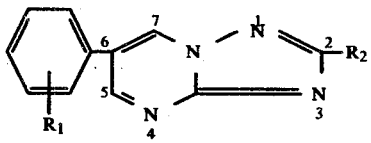

| Example | Compound | Procedure used | $R_1$ | $R_2$ | m.p. °C. | Crystallization Solvent |
|---|---|---|---|---|---|---|
| 31 | 6-(p-Chlorophenyl)-2-methyl-1,2,4-triazolo[1,5-a]pyrimidine | Example 30 | p-Cl | $CH_3$ | 257–260 | Glacial Acetic Acid |
| 32 | 6-(p-Fluorophenyl)-1,2,4-triazolo[1,5-a]pyrimidine | Example 30 | p-F | H | 220–223 | Glacial Acetic Acid |
| 33 | 6-(p-Fluorophenyl)-2-methyl-1,2,4-triazolo-[1,5-a]pyrimidine | Examples 29 and 30 | p-F | $CH_3$ | 229≧235 | Glacial Acetic Acid |
| 34 | 6-(m-Chlorophenyl)-1,2,4-triazolo[1,5-a]pyrimidine | Example 30 | m-Cl | H | 188–194 | Glacial Acetic Acid |
| 35 | 6-(m-Chlorophenyl)-2-methyl-1,2,4-triazolo[1,5-a]pyrimidine | Example 29 | m-Cl | $CH_3$ | 251–252 | Ethanol |
| 36 | 6-(o-Chlorophenyl)-1,2,4-triazolo[1,5-a]pyrimidine | Example 29 | o-Cl | H | 157–159 | Acetone/Hexane |
| 37 | 6-(m-Trifluoromethylphenyl)-1,2,4-triazolo[1,5-a]pyrimidine | Example 29 | m-$CF_3$ | H | 168–170 | Acetone/Hexane |
| 38 | 2-Methyl-6-(m-trifluoromethylphenyl)-1,2,4-triazolo[1,5-a]pyrimidine | Example 29 | m-$CF_3$ | $CH_3$ | 205–206 | Acetone/Hexane |
| 39 | 6-(m-Fluorophenyl)-2-methyl-1,2,4-triazolo[1,5-a]pyrimidine | Example 29 | m-F | $CH_3$ | 229–230 | Ethanol/Hexane |
| 40 | 6-(m-Fluorophenyl)-1,2,4-triazolo[1,5-a]pyrimidine | Example 29 | m-F | H | 201–203 | Acetone |

EXAMPLE 41

3-Dimethylamino-3'-(trifluoromethyl)acrylophenone

A reaction mixture of 50 g. of m-trifluoromethylacetophenone and 50 ml. of dimethylformamide dimethylacetal is refluxed for 16 hours under anhydrous conditions and then evaporated in vacuo to a thick orange-red oil. Hexane is added, the mixture is chilled and the desired product is collected by filtration as yellow crystals, m.p. 60.5°–62° C.

To a solution of 60 g. of ethylethoxymethylene malonitrile in 400 ml. of absolute ethanol is added 22 g. of hydrazine hydrate. The exothermic mixture gives a clear solution. After standing, the solution is concentrated to a gum. Trituration with ether gives the desired product, m.p. 97°–99° C.

EXAMPLE 45

3-Dimethylamino-2'-(trifluoromethyl)acrylophenone

A mixture of 35 g. of o-trifluoromethylacetophenone in 35 ml. of dimethylformamide dimethylacetal is refluxed for 8 hours under anhydrous conditions and then evaporated to a yellow oil. Bulb to bulb distillation gives the desired product as a thick yellow oil.

EXAMPLE 46

3-Dimethylamino-3'-methoxyacrylophenone

A mixture of 25 g. of m-methoxyacrylophenone and 25 ml. of dimethylformamide dimethylacetal is refluxed for 12 hours. Removal of any volatile material in vacuo gives a thick oil. Bulb to bulb distillation gives the desired product.

EXAMPLE 47

3-Dimethylamino-2'-fluoroacrylophenone

A mixture of 25.0 g. of o-fluoroacetophenone and 35 ml. of dimethylformamide dimethylacetal is refluxed for 16 hours. Evaporation gives a thick oil which is dissolved in methylene chloride and passed through a short column of hydrous magnesium silicate. Evaporation of the solvent gives 34.2 g. of the desired compound as an oil.

EXAMPLE 48

3-Dimethylamino-4'-fluoroacrylophenone

A mixture of 5.0 g. of p-fluoroacetophenone and 10 ml. of dimethylformamide dimethylacetal is refluxed for 4 hours. Evaporation gives an oil which crystallizes with the addition of hexane to give the product, m.p. 83.5°–84° C.

EXAMPLE 49

2'-Chloro-3-dimethylaminoacrylophenone

A mixture of 25 g. of o-chloroacetophenone and 25 ml. of dimethylformamide dimethylacetal is refluxed for 16 hours. Evaporation gives a thick red-brown oil which is dissolved in methylene chloride and this solution passed through a hydrous magnesium silicate column. Evaporation of solvent gives an oil which is then purified by bulb to bulb distillation.

EXAMPLE 50

3'-Chloro-3-dimethylaminoacrylophenone

A mixture of 50.0 g. of p-chloroacetophenone and 50 ml. of dimethylformamide dimethylacetal is refluxed for 6 hours. Evaporation gives a thick oil which crystallized on the addition of hexane, m.p. 68°–70° C.

EXAMPLE 51

4'-Chloro-3-dimethylaminoacrylophenone

A mixture of 10.0 g. of p-chloroacetophenone and 25 ml. of dimethylformamide dimethylacetal is refluxed for 3 hours. Evaporation gives a thick oil which crystallized with the addition of hexane, to give the product, m.p. 78.5°–80.5° C. Recrystallization from methylene chloride and hexane provides the product of the Example as crystals, m.p. 83°–84° C.

EXAMPLE 52

3-Dimethylamino-2'-methoxyacrylophenone

A mixture of o-methoxyacetophenone and dimethylformamide dimethylacetal is reacted as described in Example 51 to give the product of the Example.

EXAMPLE 53

3-Dimethylamino-4'-methoxyacrylophenone

A mixture of 25 g. of p-methoxyacetophenone and 25 ml. of dimethylformamide dimethylacetal is refluxed for 9 hours. Evaporation gives an oil which crystallized on the addition of hexane. Recrystallization from methylene chloride and hexane gives the desired compound, m.p. 92°–95° C.

EXAMPLE 54

7-Phenyl-1,2,4-triazolo[1,5-a]pyrimidine

A mixture of 5.25 g. of 3-dimethylaminoacrylophenone and 2.52 g. of 3-amino-1,2,4-triazole in 25 ml. of glacial acetic acid is refluxed for 4 hours. Evaporation gives a solid which is treated with a saturated sodium bicarbonate solution and dissolved in methylene chloride. This solution is passed through a short column of a hydrous magnesium silicate. Addition of hexane to a refluxing solution of the eluent gives crystals of the desired compound, m.p. 143°–144° C. K. Shirakawa, Yakugaku Zasshi 80, 956 (1960) cites melting point 140° C. for the compound assigned this structure but prepared by a different route.

EXAMPLE 55

7-(m-Trifluoromethylphenyl)-1,2,4-triazolo[1,5-a]pyrimidine

A mixture of 3.36 g. of 3-amino-1,2,4-triazole and 9.66 g. of 3-dimethylamino-3'-trifluoromethylacrylophenone in 50 ml. of glacial acetic acid is refluxed for 5 hours. The resulting mixture is worked up as described in Example 54 to give the product of the Example, m.p. 158.5°–159.5° C.

EXAMPLE 56

2-Methyl-7-(m-trifluoromethylphenyl)-1,2,4-triazolo[1,5-a]pyrimidine

A mixture of 0.49 g. of 3-amino-5-methyl-1,2,4-triazole and 1.26 g. of 3-dimethylamino-3'-trifluoromethylacrylophenone in 25 ml. of glacial acetic acid refluxed for 16 hours. The resulting mixture is worked up as described in Example 54 to give the product of the Example, m.p. 153°–154° C.

EXAMPLE 57

2-Ethyl-7-(m-trifluoromethylphenyl)-1,2,4-triazolo[1,5-a]pyrimidine

A mixture of 2.24 g. of 3-amino-5-ethyl-1,2,4-triazole and 4.86 g. of 3-dimethylamino-3'-trifluoromethylacrylophenone in 50 ml. of glacial acetic acid is refluxed for 16 hours. The resulting mixture is worked up as described in Example 54 to give the product of the Example, m.p. 132°–134° C.

EXAMPLE 58

7-(o-Fluorophenyl)-1,2,4-triazolo[1,5-a]pyrimidine

A mixture of 4.20 g. of 3-amino-1,2,4-trizazole and 9.65 g. of 3-dimethylamino-3'-fluoroacrylophenone in 25 ml. of glacial acetic acid is refluxed for 4 hours. The resulting mixture is worked up as described in Example 54 to give the product of the Example, m.p. 168.5°–172.5° C.

EXAMPLE 59

7-(o-Trifluoromethylphenyl)-1,2,4-triazolo[1,5-a]pyrimidine

A mixture of 1.68 g. of 3-amino-1,2,4-triazole and 4.86 g. of 3-dimethylamino-2'-trifluoromethylacrylophenone in 25 ml. of glacial acetic acid refluxed for 16 hours. The resulting mixture is worked up as described in Example 54 to yield the product of the Example, m.p. 149°–151° C.

EXAMPLE 60

7-(m-Methoxyphenyl)-1,2,4-triazolo[1,5-a]pyrimidine

A mixture of 2.54 g. of 3-amino-1,2,4-triazole and 6.15 g. of 3-dimethylamino-3′-methoxyacrylophenone in 25 ml. of glacial acetic acid is refluxed for 6 hours. The resulting mixture is worked up as described in Example 54 to give the product of the Example, m.p. 163°–165° C.

EXAMPLE 61

7-Hydroxy-5-(m-trifluoromethylphenyl)-1,2,4-triazolo[1,5-a]pyrimidine

A mixture of 1.64 g. of 3-amino-1,2,4-triazole and 5.10 g. of ethyl m-trifluoromethylbenzoyl acetate is inserted into an oil bath heated to 180° C. After much gas evolution, the liquid mass solidifies and is kept at this temperature for one hour and is cooled. Hexane is added and the desired compound collected by filtration.

EXAMPLE 62

7-Chloro-5-(m-trifluoromethylphenyl)-1,2,4-triazolo[1,5-a]pyrimidine

A mixture of 3.50 g. of 7-hydroxy-5-(m-trifluoromethylphenyl)-1,2,4-triazolo[1,5-a]pyrimidine and 25 ml. of phosphorus oxychloride is refluxed for 6 hours. The excess reagent is removed by evaporation; ice is added and 1 N sodium hydroxide is added until the aqueous phase is basic to indicator paper. The compound is extracted with methylene chloride and the solution passed through a short column of a hydrous magnesium silicate. Evaporation of eluent gives the desired compound as a light yellow solid.

EXAMPLE 63

5-(m-Trifluoromethylphenyl)-1,2,4-triazolo[1,5-a]pyrimidine

A mixture of 0.30 g. of 7-chloro-5-(m-trifluoromethylphenyl)-1,2,4-triazolo[1,5-a]pyrimidine, 0.10 g. of 10% palladium on charcoal catalyst, and 0.09 g. of anhydrous sodium acetate in 100 ml. of absolute ethanol is hydrogenated at 10 lbs. pressure for 30 minutes. The solution is filtered through a Celite pad and then evaporated to dryness. A methylene chloride solution of this material is washed with an aqueous saturated sodium bicarbonate solution. The organic layer, after drying with anhydrous magnesium sulfate, is passed through a short pad of hydrous magnesium silicate. The eluent is refluxed and the gradual addition of hexane caused the desired compound to crystallize to give product, m.p. 201°–202° C.

EXAMPLE 64

2-Mercapto-4-phenylpyrimidine

A mixture of 17.5 g. of 3-dimethylaminoacrylophenone and 30.44 g. of thiourea is intimately mixed and fused at 180°–190° C. for one hour. The mixture is cooled and water is added and the desired compound is recovered by filtration, m.p. 203°–205° C.

EXAMPLE 65

2-Mercapto-4-(m-trifluoromethylphenyl)pyrimidine

A mixture of 12.2 g. of 3-dimethylamino-3′-trifluoromethylacrylophenone and 15.2 g. of thiourea is heated at 180°–190° C. for 2 hours. The cooled crude reaction mixture is dissolved in 200 ml. of 1 N sodium hydroxide solution and is treated with activated charcoal and filtered. The filtered solution is acidified with 1 N hydrochloric acid and the desired compound is collected by filtration, m.p. 200°–205° C.

EXAMPLE 66

2-Methylthio-4-phenylpyrimidine

A solution of 3.5 g. of 2-mercapto-4-phenylpyrimidine in 50 ml. of 1 N sodium hydroxide is cooled to near 0° C. and 2.94 g. of methyl iodide is added. After stirring at room temperature for 2 hours, the product is recovered by filtration. Recrystallization from methylene chloride-hexane affords the desired compound, m.p. 87°–89° C.

EXAMPLE 67

2-Methylthio-4-(m-trifluoromethylphenyl)pyrimidine

A solution of 4.75 g. of 2-mercapto-4-(m-trifluoromethylphenyl)pyrimidine in 50 ml. of 1 N sodium hydroxide is cooled to near 0° C. in an ice bath and 2.90 g. of methyliodide is added. After the reaction mixture is allowed to warm to room temperature, the product is removed by filtration, m.p. 89°–90° C.

EXAMPLE 68

2-Methylsulfonyl-4-phenylpyrimidine

A solution of 2.02 g. of 2-methylthio-4-phenylpyrimidine in 50 ml. of methylene chloride is cooled in an ice bath with 4.33 g. of m-chloroperbenzoic acid being added portionwise. After standing at room temperature overnight, the reaction mixture is washed with a saturated potassium carbonate solution, separated, and dried over anhydrous sodium sulfate. The solution is passed through a short pad of hydrous magnesium silicate absorbent and the eluent is refluxed on a steam bath with addition of hexane until crystallization is induced. On cooling the desired compound is removed by filtration, m.p. 135.5°–137° C. Rec. Trav. Chim. 93, 375 (1974), m.p. 135°–135.5° C.

EXAMPLE 69

2-Methylsulfonyl-4-(m-trifluoromethylphenyl)pyrimidine

A solution of 2.70 g. of 2-methylthio-4-(m-trifluoromethylphenyl)pyrimidine in 50 ml. of methylene chloride is treated with 4.32 g. of m-chloroperbenzoic acid and the product is obtained as described in Example 68, m.p. 152°–153° C.

EXAMPLE 70

2-Hydrazino-4-phenylpyrimidine

A solution of 1.0 g. of 2-methylsulfonyl-4-phenylpyrimidine in 25 ml. of absolute ethanol is treated with 0.34 g. of 95% hydrazine. The reaction mixture is refluxed for 6 hours and then cooled and the desired product is obtained by filtration, m.p. 116°–118° C.

EXAMPLE 71

2-Hydrazino-4-(m-trifluoromethylphenyl)pyrimidine

A solution of 6.0 g. of 2-methylsulfonyl-4-(m-trifluoromethylphenyl)pyrimidine in 75 ml. of absolute ethanol is treated with 1.9 g. of 95% hydrazine and is refluxed for 8 hours. Isolation as in the previous example gives the desired compound, m.p. 103°–106° C.; resolidifies and melts at 120°–122° C.

EXAMPLE 72

7-Phenyl-1,2,4-triazolo[4,3-a]pyrimidine

A mixture of 2.0 g. of 2-hydrazino-4-phenylpyrimidine and 25 ml. of triethyl orthoformate is refluxed for 6 hours. On cooling the desired compound is removed by filtration, m.p. 232°–234° C. [This compound is cited J. Chem. Soc. Japan, Ind. Chem. Sect. 58, 440 (1955) as having m.p. 192° C. No description or preparation procedures are given.]

EXAMPLE 73

7-(m-Trifluoromethylphenyl)-1,2,4-triazolo[4,3-a]pyrimidine

A mixture of 2.0 g. of 2-hydrazino-4-(m-trifluoromethylphenyl)pyrimidine and 25 ml. of triethyl orthoformate is refluxed for 8 hours. Cooling gives the desired compound, m.p. 202°–203° C.

EXAMPLE 74

3-Methyl-7-phenyl-1,2,4-triazolo[4,3-a]pyrimidine

A mixture of 2.0 g. of 2-hydrazino-4-phenylpyrimidine and 25 ml. of triethyl orthoacetate is refluxed for 8 hours. On cooling the desired compound is removed by filtration, m.p. 303°–306° C.

EXAMPLE 75

3-Methyl-7-(m-trifluoromethylphenyl)-1,2,4-triazolo[4,3-a]pyrimidine

A mixture of 1.0 g. of 2-hydrazino-4-(m-trifluoromethylphenyl)pyrimidine and 25 ml. of triethyl orthoacetate is refluxed for 12 hours. On cooling the desired compound is isolated by filtration, m.p. 232°–234° C.

EXAMPLE 76

3-Ethyl-7-phenyl-1,2,4-triazolo[4,3-a]pyrimidine

A mixture of 1.55 g. of 2-hydrazino-4-phenylpyrimidine and 25 ml. of triethyl orthopropionate is refluxed for 6 hours. On cooling the desired compound is obtained by filtration, m.p. 246°–247° C.

EXAMPLE 77

3-Ethyl-7-(m-trifluoromethylphenyl)-1,2,4-triazolo[4,3-a]pyrimidine

A mixture of 1.50 g. of 2-hydrazino-4-(m-trifluoromethylphenyl)pyrimidine and 25 ml. of triethyl orthopropionate is refluxed for 8 hours. On cooling the desired compound is obtained by filtration, m.p. 223°–224° C.

We claim:
1. A compound consisting of the formula:

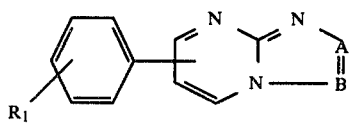

wherein —A=B— is selected from the group consisting of

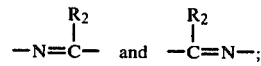

$R_1$ selected from the group consisting of chloro, fluoro, trifluoromethyl, lower alkoxy ($C_1$–$C_3$) and $R_2$ is selected from the group consisting of hydrogen and lower alkyl ($C_1$–$C_3$).

2. The compound in accordance with claim 1, 7-(m-trifluoromethylphenyl)-1,2,4-triazolo[1,5-a]pyrimidine.

3. The compound in accordance with claim 1, 2-methyl-7-(m-trifluoromethylphenyl)-1,2,4-triazolo[1,5-a]pyrimidine.

4. The compound in accordance with claim 1, 6-(p-fluorophenyl)-2-methyl-1,2,4-triazolo[1,5-a]pyrimidine.

5. The compound in accordance with claim 1, 6-(p-fluorophenyl)-3-methyl-1,2,4-triazolo[4,3-a]pyrimidine.

6. The compound in accordance with claim 1, 6-(o-chlorophenyl)-1,2,4-triazolo[1,5-a]pyrimidine.

7. The compound in accordance with claim 1, 7-(o-fluorophenyl)-1,2,4-triazolo[1,5-a]pyrimidine.

8. The compound in accordance with claim 1, 6-(p-chlorophenyl)-2-methyl-1,2,4-triazolo[1,5-a]pyrimidine.

9. The compound in accordance with claim 1, 2-methyl-6-(m-trifluoromethylphenyl)-1,2,4-triazolo[1,5-a]pyrimidine.

10. The compound in accordance with claim 1, 3-methyl-6-(m-trifluoromethylphenyl)-1,2,4-triazolo[4,3-a]pyrimidine.

11. The compound in accordance with claim 1, 7-(m-methoxyphenyl)-1,2,4-triazolo[1,5-a]pyrimidine.

12. The compound in accordance with claim 1, 6-(m-trifluoromethylphenyl)-1,2,4-triazolo[1,5-a]pyrimidine.

13. The compound in accordance with claim 1, 6-(m-fluorophenyl)-2-methyl-1,2,4-triazolo[1,5-a]pyrimidine.

14. The compound in accordance with claim 1, 6-(m-chlorophenyl)-2-methyl-1,2,4-triazolo[1,5-a]pyrimidine.

15. The compound in accordance with claim 1, 6-(m-trifluoromethylphenyl)-1,2,4-triazolo[4,3-a]pyrimidine.

16. The compound in accordance with claim 1, 6-(m-chlorophenyl)-1,2,4-triazolo[1,5-a]pyrimidine.

* * * * *